Nov. 4, 1941. A. CUMMING Plant Pat. 492
WEIGELA PLANT
Filed July 11, 1941
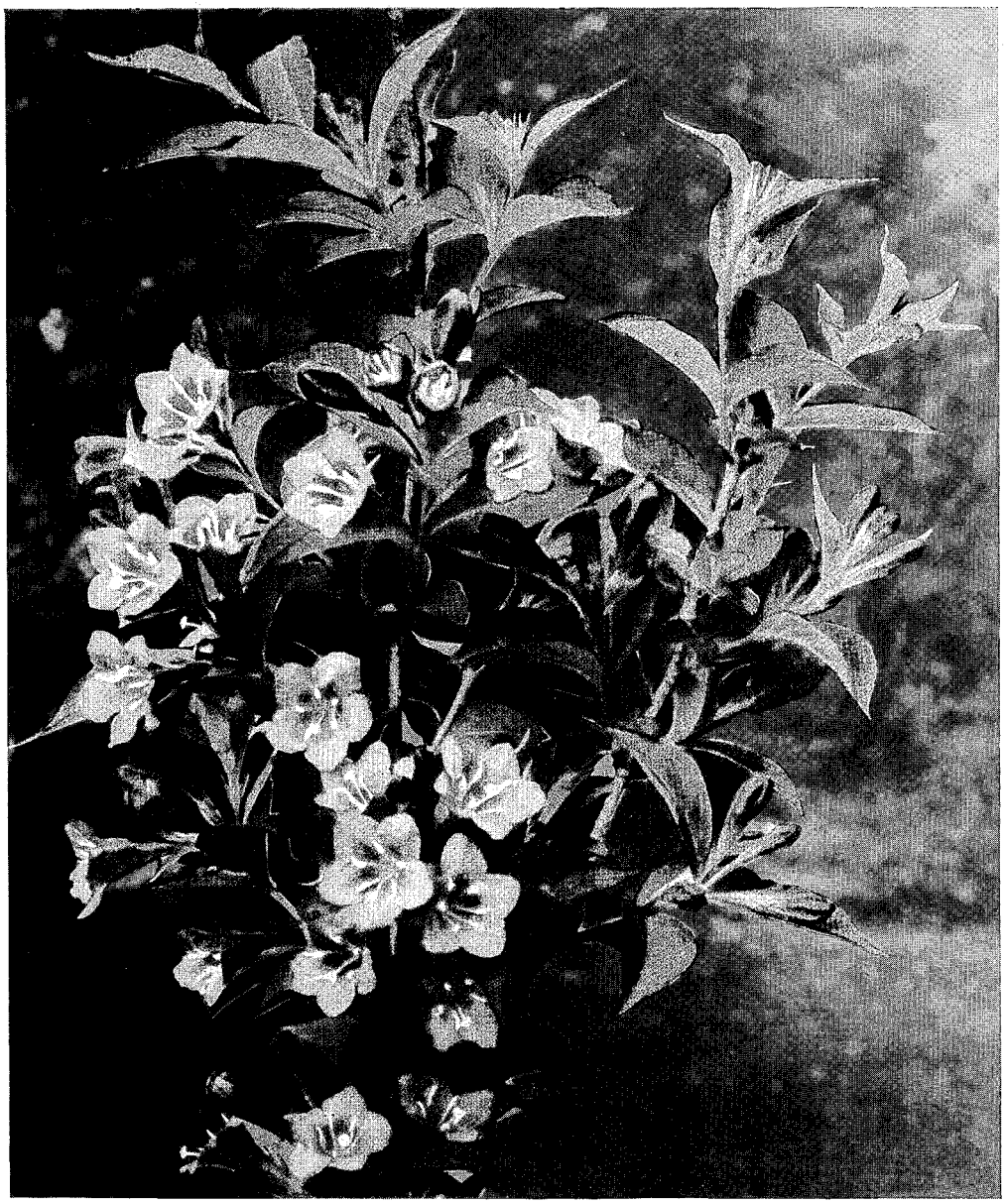
INVENTOR
Alexander Cumming
By Orville M. Kile
Plant Pat. Agt.

Patented Nov. 4, 1941

Plant Pat. 492

UNITED STATES PATENT OFFICE

492

WEIGELA PLANT

Alexander Cumming, Bristol, Conn., assignor to Bristol Nurseries, Inc., Bristol, Conn.

Application July 11, 1941, Serial No. 402,017

1 Claim. (Cl. 47—60)

My invention relates to improvements in weigela plants or bushes and consists of a new and distinct variety. The principal object of my invention was to produce an improved "Eva Rathke" weigela which would be a hardy, robust, shapely variety with flowers of a distinctive and pleasing shade of red.

My new variety is a hybrid and originated as a result of a controlled cross of *Weigela rosea* by Eva Rathke made by me at my nurseries in Bristol, Connecticut. It is more like its pollen parent, Eva Rathke, than any other variety known to me, yet there are several very pronounced differences between these two varieties. Some of these important differences are the greater vigor and hardiness, and the better balance and shapeliness of the plant of my new variety. Also it has flowers of a softer and more pleasing shade of red than those of its parent variety and these blossoms are more evenly distributed on the branch. Asexual reproduction of my new variety for a number of years has shown its qualities to be permanently fixed.

The original plant of my new variety is now eight feet high and approximately the same distance across at its base. This is probably its maturity height. However, a plant four years old is now about six feet high and the same distance through at the base.

The original illustrations, which are filed as a part of this application, show in approximately natural size and color, a portion of a branch of my new weigela variety.

Following is a detailed description of the plant and flower of my new variety. Color plate references indicate Ridgway's Color Standards and Nomenclature. Where no plate references are given, the usual dictionary meaning is intended.

*The plant*

Growth habit: Well balanced and compact, requiring little pruning to keep it in good shape. No die-back or uneven growth occurs. Growth very robust and vigorous. The original specimen, which is more than ten years old, has attained a height of eight feet and a similar breadth at its base.

Hardiness: Much more hardy than its parents and other varieties of weigela known to me. Does not winter-kill in Connecticut even during the early stages of its growth. Excellent reports from Vermont and other difficult regions fully substantiate the claim to unusual hardiness.

Blooming habit: Very profuse bloomer. Blossoms appear singly or in clusters and are evenly dispersed over the entire plant.

Blooming dates: Normal blooming season begins about June 1st in this climate, with the entire plant covered with bloom and the display continuing throughout the month. Thereafter the plant flowers sporadically until October.

Foliage: Profuse. Slender and considerably smaller than foliage of most weigela varieties. Very rich green color.

*Size.*—Length of mature leaves is about 2¼ inches; breadth is ¾ to ⅞ inch.

*Shape.*—Elliptical, with very long point.

*Color.*—Mature leaves are approximately Cerro Green (Pl. V) on the upper surface, and Light Cress Green (Pl. XXXI) on the under surface. Younger leaves are lighter and brighter than the mature leaves.

Stems: Main stems stiff; woody; strong; light tan in color. Tip stems soft and with reddish tinge.

*The flower*

Bud:

*Size.*—Just before opening, bud is approximately ¾ inch long.

*Color.*—Between Carmine and Ox-blood Red (Pl. I).

*Peduncle.*—Short; reddish-tinged.

Blossom:

*Size.*—Averages 1 inch long and 1 inch across the fully opened flower.

*Shape.*—Trumpet-like, with five lobes or petals which spread almost flat.

*Color.*—Neither Ridgway's nor R. H. S. color charts gives the true color of this flower. In popular dictionary terms it might be described by saying that the buds and newly opened flowers are rich, deep garnet (nearest in Ridgway's being between Carmine and Ox-blood Red, Pl. I), changing in a few days to soft silvery rose (nearest in Ridgway's being Spinel Pink, Pl. XXVI). As the garnet disappears from the throat, in many instances a long yellow stripe appears below one of the lobes.

*Fragrance.*—The slight scent is peculiar but pleasant.

Reproductive organs:

*Stamens.*—There are five stamens which have pink to rose-colored filaments lying close to the throat and attached to it for about one-half their length. Each filament is topped by a large, cream-colored anther.

*Pistil.*—A single pistil rises ⅛ to ⅜ inch higher than the stamens. Its style is white and is topped by a large, cream-colored stigma.

Having thus disclosed my invention, I claim:

The new and distinct variety of weigela plant herein shown and described, characterized particularly by its hardy, robust and balanced growth; its habit of blooming with even distribution of blossoms; its particularly rich, green foliage; and its flowers of distinctive color of a soft, pleasing shade of red as indicated.

ALEXANDER CUMMING.